(12) United States Patent
Glaug et al.

(10) Patent No.: US 6,369,290 B1
(45) Date of Patent: Apr. 9, 2002

(54) TIME RELEASE ODOR CONTROL COMPOSITION FOR A DISPOSABLE ABSORBENT ARTICLE

(75) Inventors: Frank S. Glaug, Chester Springs, PA (US); Andrew Waksmundzki, Jackson, NJ (US)

(73) Assignee: Tyco Healthcare Retail Services AG, Schaffhausen (CH)

( * ) Notice: Subject to any disclaimer, the term of this patent is extended or adjusted under 35 U.S.C. 154(b) by 0 days.

(21) Appl. No.: 09/506,299

(22) Filed: Feb. 17, 2000

(51) Int. Cl.⁷ .................... A61F 13/15; A61K 7/32; A61K 9/50
(52) U.S. Cl. ............ 604/359; 604/367; 424/65; 424/490; 424/717; 424/493
(58) Field of Search .................. 604/359, 361, 604/367, 385.01, 385.23; 424/65, 490, 717, 493, 499; 512/4

(56) References Cited

U.S. PATENT DOCUMENTS

| | | | |
|---|---|---|---|
| 3,691,271 A | 9/1972 | Charle et al. ............... 424/28 |
| 4,186,743 A | * 2/1980 | Steiger ..................... 128/284 |
| 5,037,412 A | 8/1991 | Tanzer et al. .............. 604/359 |
| 5,103,500 A | 4/1992 | Nager et al. ................... 2/56 |
| 5,364,380 A | * 11/1994 | Tanzer et al. .............. 604/359 |
| 5,407,442 A | 4/1995 | Karapasha ................. 604/359 |
| 5,429,628 A | 7/1995 | Trinh et al. ................ 604/359 |
| 5,482,702 A | * 1/1996 | Murphy et al. .............. 424/65 |
| 5,582,603 A | * 12/1996 | Difilippantonio et al. ... 604/380 |
| 5,591,146 A | 1/1997 | Hasse ........................ 604/359 |
| 5,733,272 A | 3/1998 | Brunner et al. ............ 604/359 |
| 5,769,832 A | 6/1998 | Hasse ........................ 604/359 |
| 5,769,833 A | 6/1998 | Hasse ........................ 604/359 |
| 5,827,913 A | * 10/1998 | Baetzold et al. ............ 523/210 |
| 5,861,144 A | * 1/1999 | Peterson et al. ............. 424/65 |
| 5,944,704 A | * 8/1999 | Guarracino et al. ........ 604/359 |

* cited by examiner

Primary Examiner—John G. Weiss
Assistant Examiner—Jamisue Webb
(74) Attorney, Agent, or Firm—Howson & Howson

(57) ABSTRACT

A disposable absorbent article is provided with a odor control powder which is unscented in a dry state and releases a burst of fragrance when wetted, such as by human waste. The powder contains a relatively small amount of fragrance oil, such as 0.5% to 4% by weight, to prevent skin irritation to the wearer. The small amount of fragrance oil is microencapsulated in a starch which constitutes from about 50% to 90%, and preferably about 70%, of the total weight of the particles. Sodium bicarbonate is also included in the particulate odor control material in an amount ranging from 5.0% to 45%, and preferably about 25% by weight, of the total weight of the particles. The sodium bicarbonate promotes skin wellness by controlling the pH levels of the fragrance oil, starch and human waste. A small amount of flow agent is also contained in the particulate odor control material.

23 Claims, No Drawings

TIME RELEASE ODOR CONTROL COMPOSITION FOR A DISPOSABLE ABSORBENT ARTICLE

BRIEF SUMMARY OF THE INVENTION

This invention relates to an odor control composition for use in a disposable absorbent article to reduce malodor of a body fluid such as human waste, and more particularly, the invention relates to a disposable absorbent article containing an odor control powder which is substantially unscented in an initial dry condition and which releases a fragrance when wetted. The term "substantially unscented" means that the powder is either unscented, or that any scent released by the quantity of dry powder used in a single disposable article is detectable by the ordinary observer only by close inspection, i.e. by deliberately sniffing at close range, i.e. at a distance less than about 15 cm.

Disposable absorbent articles, such as infant diapers, feminine care products, and adult incontinence products, are utilized to absorb body fluids and waste materials of infants, children and adults. Such products may be provided, for example, as briefs, undergarments, pads, guards, slip-ons and inserts, and may, or may not, contain odor control and/or masking agents. Typically, a disposable absorbent article which does not have an odor control/masking agent is classified as "unscented" or "hypoallergenic".

Sodium bicarbonate, which is also known as baking soda, has been utilized as a material to control odors in various consumer products. However, its deodorizing efficacy in an absorbent article containing urine and/or fecal waste is believed to be very limited. An example of an absorbent article containing a deodorizing mixture utilizing sodium bicarbonate as a basic odor absorbing material is provided by U.S. Pat. No. 5,037,412 to Tanzer et al. The Tanzer patent states at column 5, lines 30–39, that sodium bicarbonate forms 25 to 75% by weight, and preferably, 40 to 65% by weight, of the deodorizing mixture. Another odor control material that is used in absorbent articles is a synthetic zeolite which has micro-pores capable of trapping vapors. Fluids, for instance, urine, tend to obstruct the micro-pores of the synthetic zeolite and cause the pores to become ineffective in trapping vapors. Thus, a synthetic zeolite is typically only successful when utilized with respect to a malodor that is not associated with a fluid. Examples of the use of a synthetic zeolite as an odor-controlling composition is provided by U.S. Pat. No. 5,407,442 to Karapasha and U.S. Statutory Invention Registration No. H1579 to Furio.

Fragrance oils have been used as odor masking agents in disposable absorbent articles which are typically identified as "deodorant", or "scented", articles and which have been successful at masking odors associated with human waste. However, since fragrance oils contain organic solvents, they tend to cause skin irritation and rashes on wearers having sensitive skin. In addition, fragrance oils are relatively expensive and dissipate over time, so that a disposable absorbent article having a fragrance oil has a relatively short shelf life insofar as its deodorizing function is concerned. The use of a large amount of fragrance oil is required to achieve a long shelf life because the fragrance dissipates over time. Another problem with the use of fragrance oils is that different consumers prefer different fragrances, and it is difficult to identify a specific scent which is generally satisfactory to a broad range of consumers.

Fragrance oils have been microencapsulated in moisture activated particles to eliminate fragrance dissipation and to extend shelf life. For instance, U.S. Pat. No. 5,733,272 to Brunner et al. and U.S. Pat. No. 5,429,628 to Trinh et al. disclose the use of fragrance oils, or perfume, in diapers and other disposable absorbent articles. The perfume is encapsulated and moisture-activated so that, when the material is wetted, the perfume is released to mask the odor with a pleasant burst of fragrance. The content of perfume in each microcapsule is in the range of 5% to 15% by weight.

U.S. Pat. No. 5,103,500 to Nager et al. and U.S. Pat. No. 3,691,271 to Charle et al. also disclose disposable absorbent articles having time release microcapsules. The Nager patent discloses a garment shield which releases a fragrance when wetted with perspiration, and Example 1 disclosed in the Charle patent discloses a deodorant powder which releases a perfume when wetted.

U.S. Pat. Nos. 5,591,146, 5,769,833 and 5,769,832, to Hasse, disclose disposable absorbent articles having microcapsules which release a perfume upon the removal of a release liner.

While the aforementioned odor control and/or masking agents used in disposable absorbent articles may be satisfactory for their intended purposes, there is a need for an improved odor control composition for a disposable absorbent article which is capable of controlling malodor associated with human waste and which is economical to produce. The odor control composition should enable the disposable absorbent article to be substantially unscented in an initial dry state, provide a burst of fragrance when wetted, and have a relatively long shelf life. In addition, the odor control composition should not be irritating to the skin of the wearer and should be capable of neutralizing the pH levels of the moisture-activated perfume and the human waste.

Therefore, the principal object of this invention is to provide a novel odor control composition for a disposable absorbent article which is capable of masking malodor associated with human waste and which requires the use of a relatively small amount of fragrance oil so that the disposable absorbent article is relatively inexpensive to manufacture and so that the odor control composition does not irritate sensitive skin or cause rashes. The absorbent article should be initially unscented and provide a pleasing unisex fragrance when activated. Although only a small amount of fragrance oil is used, the disposable absorbent article and its associated deodorant function should have a long shelf life.

The invention addresses the foregoing objects by providing an odor control composition comprising a powder which is unscented in an initial dry condition and which, when wetted, releases a fragrance. Each powder particle includes a fragrance oil microencapsulated within a starch and contains sodium bicarbonate. Preferably, the odor control composition is utilized in a disposable absorbent article, and each powder particle has about 0.5 to 4% by weight of fragrance oil, about 5 to 45% by weight of sodium bicarbonate, and about 50 to 90% by weight of a starch. In addition, each particle includes about 1 to 4% of a flow agent. The total amount of odor control composition to be utilized in a disposable absorbent article depends on the type, size and purpose of the product. For instance, smaller products such as sanitary napkins will utilize a smaller amount of odor control composition than an adult brief. In the case of an adult brief, for example, the amount of odor control composition should be in the range of about 0.1 to 30 grams, preferably about 1.0 gram.

DETAILED DESCRIPTION

The odor control composition of the invention can be utilized in any disposable absorbent article, but is particularly suited for use in adult briefs/diapers. Adult briefs, which are similar to infant diapers, include an absorbent core covered on an inner side with a fluid-pervious cover sheet, or acquisition layer, and covered on an opposite outer side with a fluid-impervious, or hydrophobic, backing. Preferably, the odor control composition of the invention is provided in powder form and is applied on the absorbent core adjacent the fluid pervious sheet or adjacent the fluid impervious or hydrophobic backing. Alternatively, the powder can be dispersed within the absorbent core, can be located within a multi-ply material utilized in the disposable absorbent article, or can be applied to the disposable absorbent article in other ways known in the art.

The odor control powder includes the use of a fragrance oil to mask a malodor, such as caused by human waste. The fragrance oil is microencapsulated in a starch so that the powder is substantially unscented until wetted at which time it releases a burst of fragrance. Such a composition is particularly useful in an adult brief/diaper since most wearers prefer a generally unscented product which does not attract attention to the use of the product. The fragrance is only released at a time when a malodor requires masking and when the brief/diaper requires changing.

The use of a microencapsulated fragrance oil makes it possible to use a lesser amount of fragrance oil to provide the required deodorant function. Reduced amounts of fragrance oil promotes product safety and provides a disposable absorbent article which is relatively inexpensive to produce. The likelihood of skin irritation is reduced because the amount of fragrance oil is reduced and because the fragrance oil is not exposed to the skin of the wearer until the presence of a liquid, such as urine, causes the release of the fragrance. The use of less fragrance oil, in turn, significantly reduces the cost of manufacture of the disposable absorbent article.

The microencapsulated particles of the odor control powder also include an amount of sodium bicarbonate which promotes skin wellness. When the odor control powder is wetted and the fragrance is released, the sodium bicarbonate neutralizes the pH levels of the fragrance oil, the starch and the human waste.

The microencapsulated particles are capable of being produced in an economical and efficient process. A starch is mixed in water in a large vat until will blended, and then sodium bicarbonate is added to the starch slurry. The sodium bicarbonate should be added slowly to the slurry since the sodium bicarbonate has a foaming reaction with the water and can cause the vat to overflow. In addition, only a limited defined amount of sodium bicarbonate, preferably not more than about 45% by weight, can be added to the slurry because larger amounts of the water-soluble sodium bicarbonate will be lost through effervescence, thereby reducing its actual volume in the formulation.

After the foaming reaction of the sodium bicarbonate stabilizes, the fragrance oil is added to the slurry and the slurry is well blended and transferred to a spray dry injection vat. The slurry is metered and injected at a high velocity into a cyclone dryer which causes the slurry to atomize into small droplets. In the cyclone, the droplets are subjected to heat to evaporate the moisture content and leave only the dried microencapsulated particulate. A flow agent, preferably a silica flow agent, is sprayed into the cyclone via a separate nozzle when the slurry droplets are being dried. The particulate material exits through the bottom of the cyclone where it is collected and later applied to disposable absorbent articles.

A novel aspect of the invention is the particular formulation of the odor control powder. The fragrance oil makes up only approximately 0.5% to 4% by weight of each particle of the powder. As stated previously, with only this small amount of fragrance oil the article is, in effect, initially unscented, but releases a sufficient amount of fragrance when activated to mask malodor. The low fragrance oil content also achieves a material cost saving in the manufacture of the article, and avoids skin irritation or rashes. Preferably, the fragrance oil is a light floral/lemon laundry softener scent, such as scent #1702–1904, available from Rely Fragrance, of Middletown, N.Y. The laundry softener scent is preferred because it is pleasing both to men and to women, is effective in reducing malodor, and is not overpowering. However, other types of fragrances can be used as well, if satisfactory to most consumers of the particular type of product in which they are used. Amounts of fragrance oil in excess of approximately 4% are unnecessary and may release too much scent. Amounts less than about 0.5% are only marginally effective in odor control.

Preferably, sodium bicarbonate makes up approximately 5% to 45% by weight of each particle of the powder. Amounts of sodium bicarbonate less than approximately 5% are only marginally effective in pH control. The use of amounts of sodium bicarbonate greater than approximately 45% results in losses due to effervescence during the microencapsulation process, and will also neutralize the fragrance released by the microencapsulated fragrance oil. In addition, excessive sodium bicarbonate can reduce the efficiency and total capacity of sodium polyacrylate superabsorbents which may be located within the absorbent core of the disposable absorbent article. Thus, care must be taken to achieve a proper balance between the use of sodium bicarbonate to control pH and the above-discussed disadvantages of the use of sodium bicarbonate. Tests have shown that a weight percentage level of about 25% of Grade 5 sodium bicarbonate, manufactured by Church & Dwight of Princeton, N.J. , provides the proper balance and the best results.

Preferably, the starch constitutes approximately 50% to 90% by weight of the formulation. The amount of starch is not critical, and the percentage of starch is primarily dependent on the amount of sodium bicarbonate present in the composition. The starch is preferably Purity Gum BE Emulsion manufactured by National Starch and Chemical, of Bridgewater, N.J.

The flow agent is preferably an amorphous silicon dioxide, manufactured by Cabot Corporation of Boston Massachusetts, and constitutes approximately 1% to 4% by weight of the formulation. Amounts of flow agent less than 1% are only marginally effective, and amounts in excess of 4% are unnecessary.

EXAMPLE

An example of a preferred formulation of each particle in the odor control powder is 3% by weight fragrance oil (Rely #1702–1904), 70% by weight starch (National Starch Purity Gum BE emulsion starch), 25% sodium bicarbonate (Church & Dwight Grade #5), and 2% flow agent (Cabot amorphous silicon dioxide). Approximately 1.0 gram of the odor control powder was applied to a medium adult brief. The odor control powder was dispensed in a continuous state directly onto the top of the absorbent core, beneath the fluid-pervious cover sheet.

The product contained a moisture indicator adhesive on the inside of the fluid-impervious backing, and it was found that the odor control powder should be kept some distance away from the moisture indicator adhesive in order to prevent the fragrance oil within the odor control powder from directly contacting the moisture indicator adhesive and activating the indicator prematurely.

The above-described odor control composition and disposable absorbent article containing an odor control powder, provide a safe, effective and economic product capable of masking malodors, particularly those caused by human waste. The fragrance is only released when activated by moisture and thereafter conspicuously masks the malodor. Since the fragrance is microencapsulated and only released when wetted, the disposable absorbent articles have a long shelf life and require a relatively small amount of fragrance. The composition also utilizes a defined amount of sodium bicarbonate to control the pH levels of the fragrance oil, starch and human waste.

Various modifications to the odor control formulation and disposable absorbent articles are contemplated. Various types of fragrance oils can be utilized, although the freshly washed clothes scent was found most desirable. The odor control powder can be applied to various locations in a continuous or intermittent pattern within the disposable absorbent article by various techniques.

While a preferred odor control formation and disposable absorbent article have been described, various modifications, alterations, and changes may be made without departing from the spirit and scope of the invention as defined in the appended claims.

We claim:

1. An odor control composition, comprising a powder which releases a fragrance when wetted, the powder consisting of particles, each particle including a fragrance oil microencapsulated within a mixture of a starch, and sodium bicarbonate.

2. An odor control composition according to claim 1, wherein the weight percentage of the fragrance oil in each of the particles is approximately 3%.

3. An odor control composition according to claim 1, wherein the weight percentage of sodium bicarbonate in each of the particles is in a range of about 5 to 45%.

4. An odor control composition according to claim 3, wherein the weight percentage of sodium bicarbonate in each of the particles is approximately 25%.

5. An odor control composition according to claim 1, wherein the weight percentage of starch in each of the particles is in a range of about 50 to 90%.

6. An odor control composition according to claim 5, wherein the weight percentage of starch in each of the particles is approximately 70%.

7. An odor control composition according to claim 1, wherein each of the particles comprises about 1 to 4% by weight of a flow agent.

8. An odor control composition according to claim 7, wherein each of the particles comprises about 2% by weight of a flow agent.

9. A disposable absorbent article comprising the odor control composition according to claim 1, wherein the amount of said odor control composition present in the absorbent article is in the range of approximately 0.1 to 30 grams.

10. A disposable absorbent article comprising the odor control composition according to claim 1, wherein the amount of said odor control composition present in the absorbent article is approximately 1.0 grams.

11. An odor control composition according to claim 1, wherein the weight percentage of the fragrance oil in each of the particles is approximately in the range of about 0.5% to 4%.

12. A time release odor control composition for a disposable absorbent article, comprising a powder which is substantially unscented when in an initial dry condition, before being wetted, and which, when wetted, releases a fragrance, the powder consisting of particles, and each of the particles comprising about 0.5 to 4% by weight of a fragrance oil, about 5 to 45% by weight of sodium bicarbonate, and about 50 to 90% by weight of a starch, the fragrance oil being microencapsulated within a mixture of the starch and the sodium bicarbonate to prevent the fragrance oil from dissipating when the powder is in said initial dry condition, before being wetted.

13. A time release odor control composition according to claim 12, wherein each particle comprises about 1 to 4% by weight of a flow agent.

14. A time release odor control composition according to claim 13, wherein each of the particles comprises approximately 3% by weight of the fragrance oil and approximately 25% by weight of sodium bicarbonate.

15. A time release odor control composition according to claim 14, wherein each of the particles comprises approximately 70% by weight of the starch and approximately 2% by weight of the flow agent.

16. A disposable absorbent article for absorbing and containing body fluids, comprising an absorbent core and an odor control powder, both located between a fluid pervious cover sheet and a fluid impervious or hydrophobic backing, the odor control powder being substantially unscented when in an initial dry condition, before being wetted, and being capable of releasing a mild fragrance when wetted, the odor control powder consisting of particle, each of the particles comprising about 0.5 to 4% by weight of a fragrance oil, about 5 to 45% by weight of sodium bicarbonate, and about 50 to 90% by weight of a starch, the fragrance oil being microencapsulated within a mixture of the starch and the sodium bicarbonate to prevent the fragrance oil from dissipating when the powder is in said initial dry condition, before being wetted.

17. A disposable absorbent article according to claim 16, wherein the odor control powder is located adjacent the fluid pervious cover sheet.

18. A disposable absorbent article according to claim 16, wherein the odor control powder is located adjacent the fluid impervious backing.

19. A disposable absorbent article according to claim 16, wherein each particle comprises about 1 to 4% by weight of a flow agent.

20. A disposable absorbent article according to claim 19, wherein each of the particles comprises approximately 25% by weight of sodium bicarbonate.

21. A disposable absorbent article according to claim 20, wherein the weight percentage of the fragrance oil in each of the particles is approximately 3%, the weight percentage of starch in each of the particles is approximately 70%, and the weight percentage of the flow agent is approximately 2%.

22. A disposable absorbent article according to claim 21, wherein the fragrance oil provides a laundry fresh scent.

23. A disposable absorbent article according to claim 22, wherein the flow agent is an amorphous silicon dioxide.

* * * * *